United States Patent [19]

Vaseen

[11] 4,223,094
[45] Sep. 16, 1980

[54] HORIZONTAL ROTATING DRUM FERMENTOR

[76] Inventor: V. A. Vaseen, 9840 W. 35th Ave., Wheatridge, Colo. 80033

[21] Appl. No.: 828,956

[22] Filed: Aug. 29, 1977

[51] Int. Cl.$^2$ .................. C12M 1/10; C12M 1/04; C12M 1/06; C12M 1/02

[52] U.S. Cl. .................. 435/312; 435/313; 435/315; 435/316

[58] Field of Search ............... 195/127, 139, 142, 146, 195/141; 47/1, 4, 58; 165/89, 90, 91, 177, 179; 366/144, 145, 147, 149, 220, 225, 228, 230; 435/312, 313, 315, 316

[56] References Cited

U.S. PATENT DOCUMENTS

| 827,148 | 7/1906 | Gordon | 195/142 |
| 2,434,519 | 1/1948 | Raskin | 165/177 |
| 2,578,166 | 12/1951 | Bill | 366/147 |
| 3,540,700 | 11/1970 | Freedman et al. | 195/127 X |
| 3,880,716 | 4/1975 | Engelbart et al. | 195/139 |
| 3,978,918 | 9/1976 | Nagatomo | 366/147 |

Primary Examiner—Thomas G. Wiseman

[57] ABSTRACT

A horizontal rotating drum fermentation apparatus having no center line shaft suitable for aerobic fermentation processes. Notably, the apparatus contains within the drum affixed to the inner walls a series of spirally oriented mixing blades adapted to be heat exchangers and cup structures which in conjunction with a discharge pipe allow for removal of solid materials. The fermentation apparatus is also fitted with an internal light source which permit photosynthetic fermentation processes to occur.

1 Claim, 3 Drawing Figures

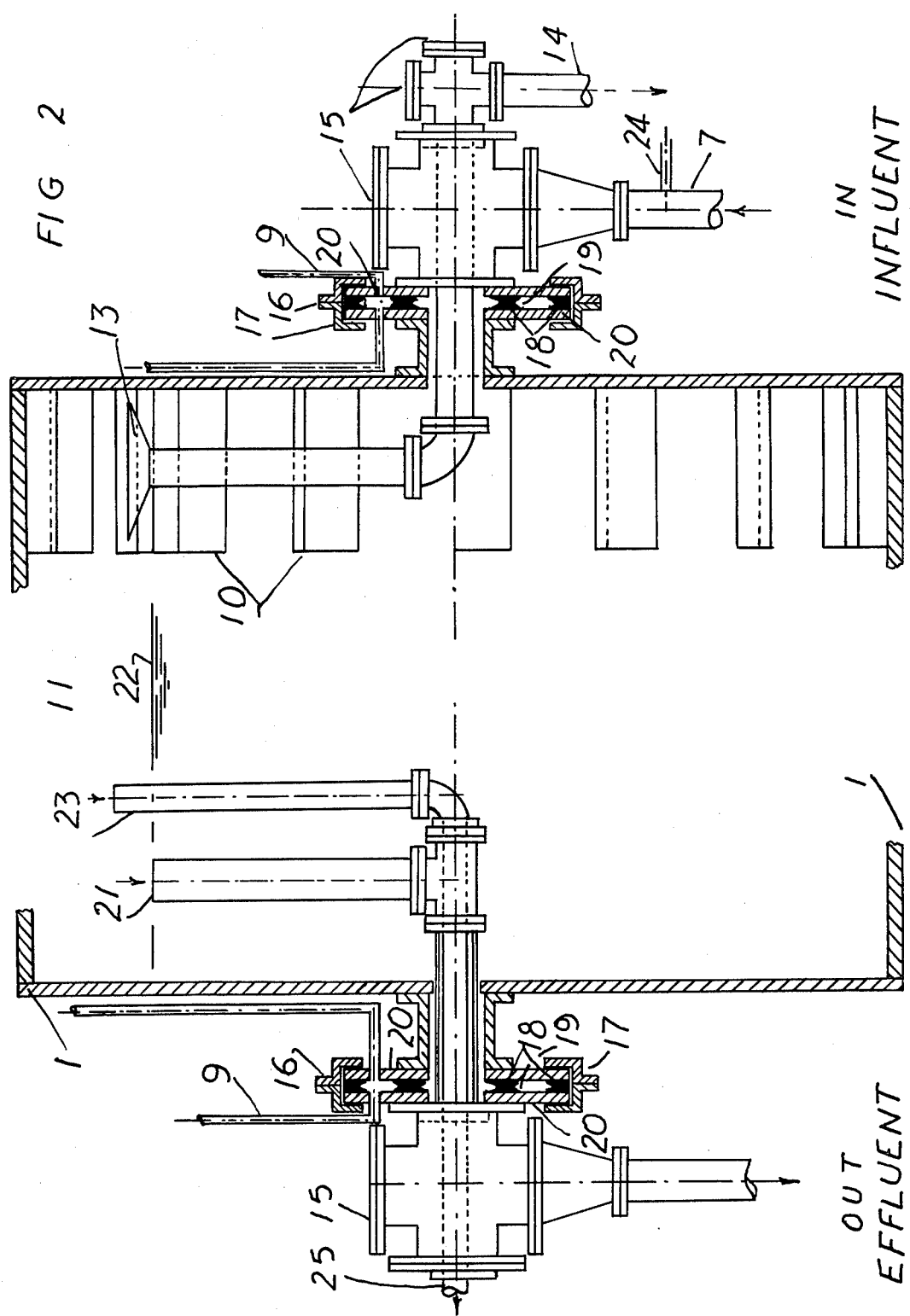

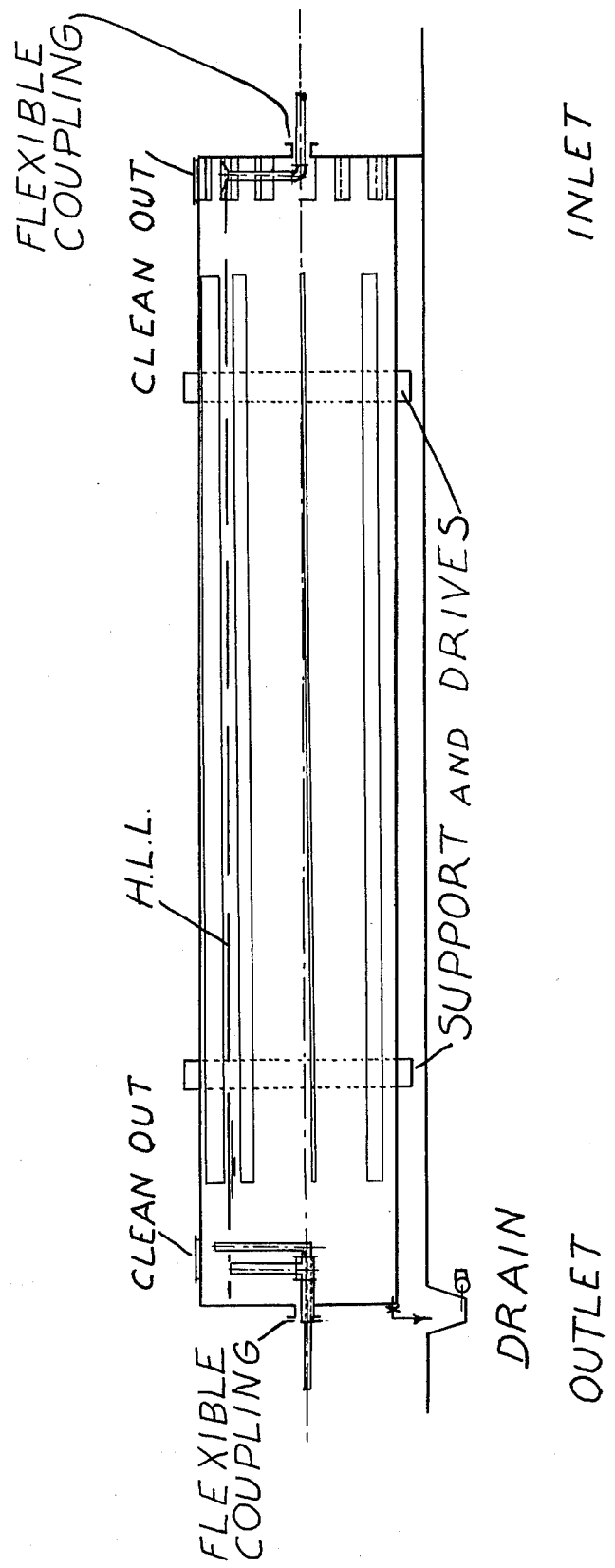

HORIZONTAL ROTATING DRUM FERMENTOR

DESCRIPTION OF THE PRIOR ART

| REFERENCES U.S. PAT. NOS. ANAEROBIC | | | |
|---|---|---|---|
| 3,933,628 | 1/20/76 | Varani | 126/271 |
| 3,077,190 | 2/1963 | Allen | 126/271 |
| 3,125,091 | 3/1964 | Sleeper, Jr. | 126/271 |
| 3,246,761 | 4/1966 | Bryan et al | 210/12X |
| 3,330,118 | 7/1967 | Biais | 126/270X |
| 3,383,309 | 6/1968 | Chandler | 210/11 |
| 3,390,672 | 7/1968 | Snelling | 126/271 |
| 3,493,494 | 2/1970 | Knibb | 210/12X |
| 3,537,267 | 11/1970 | Webb | 61/1 R X |
| 3,620,206 | 11/1971 | Harris, Jr. et al | 126/271 |
| 3,707,850 | 1/1973 | Connell et al | 61/5 X |
| 3,736,754 | 6/1973 | Azalbert et al | 61/.5 |
| 3,768,264 | 10/1973 | Best | 126/271 X |
| 3,838,199 | 9/1974 | Coe et al. | 210/2 X |

U.S. Patents pretaining to tissue, cell and callus growth in aqueous, hydroponic, single liquid media are:

1. U.S. Pat. No. 3,514,900—method for rapidly producting orchids: Everest McDade; continuation in part of application Ser. No. 622,832, Dec. 27, 1966; and Ser. No. 672,407: Aug. 11, 1967.

2. U.S. Pat. No. 3,816,960—method for growing plants; Claude Gudin; Eric Peel; with Ref's to June 1974.

U.S. Pat. No. 3,514,900—6/1970—McDade
U.S. Pat. No. 3,628,287—12/1971—Staba Et Al
U.S. Pat. No. 3,683,550—8/1972—Corlett Et Al
U.S. Pat. No. 3,704,546—12/1972—Hardy Et Al 3. U.S. Pat. No. 3,683,550—Plant culture method and product; Corlett, Jr. Et Al. August 1972.

4. U.S. Pat. No. 3,710,805—Process for producing material for smoking; Eioosuke Tamaki; Masao Kobari; Fumiharo Miyanowaki; Kunio Kato; Ko Mishida; Yukio Shimizu; January 1973.

References—Anerobic Fermentation

Mignone, N. A. "Engineers Can Exert Process Control Over Digester Imputs". Water and Sewage Works (November, 1975), 51.

Mignone, N. A. "Anaerobic Digester Design for Energy Generation." Public Works (1974), 71.

Dague, R. R., and R. E. McKinney et al. "Solids Retention in Anaerobic Waste Treatment Systems." Journal Water Pollution Control Federation, Research Supplement, 42 (1970), R-29.

Gates, W. E. et al. "A Rational Model for the Anaerobic Contact Process." Journal Water Pollution Control Federation, 39 (1967), 1951.

Lohmeyer, G. T. "A Review of Sludge Digestion." Sewage and Industrial Waste, 31 (1959), 221.

Wright, C. D. "Controlled Activated Sludge." Water and Sewage Works, Reference Number (1963).

Kraus, L. S. "Digested Sludge—An Aid to the Activated Sludge Process." Sewage Works Journal, 18 (1946), 1099.

"The PFT Supernatant Liquor Treater." Sewage Works Journal, 15 (1943), 1018. Schienz, H. E. "Controlled Digestion." Sewage Works Journal, 16 (1944), 510.

References—Cell Growth

Corn: Culture, processing, products; major feed and food crops in agriculture and food series; editor, G. E. Inglett, Ph D., Chief, Cereal Properties Laboratory; Northern Utilization Researach and Development Division, Agricultural Research Service; U.S. Dept., of Agriculture. AVI Publishing Co., Westport, Conn. (1970).

Crop Growth & Culture: Roger L. Mitchell; The Iowa State University Press; Ames, Iowa.

The Cell; Carl P. Swanson and William D. Gill; Professor in Biology The John Hopkins University. Prentice-Hall Inc.; Englewood Cliffs, N.J.

College Botany; Revised Ed.; Fuller/Tippo; University of Illinois, Holt, Rinehart and Winston; N.Y.

Plant Tissue and Cell Culture; Edited by H. E. Street (D. Sc London); Botanical Laboratories; University of Leicester; England. University of California Press; Berkeley and Los Angeles; 1973.

Agricultural Chemistry; A Reference Text; Donald E. H. Frear; Ph D., Editor; Professor of Agriculture and Biological Chemistry; Pennsylvania State College; Vol. One; Principals of Agricultural Chemistry; D. Van Nostrand Company, Inc., Toronto, New York, London.

The Awesome Worlds Within A Cell; The New Biology I.; Rick Gore.

Broad Spectrum Tissue Culture of Tobacco Callus. A broad spectrum tissue culture experiment with tobacco (nicotiana tobacum) pith tissue callus; R. A. de Fossard; Aung Myint and Edward C. M. Lee; Department of Botany; University of New England; Armidale; N. S. W. 2351; Australia: Physiol. Plant 31:125–130. 1974.

Single Cell Clones; H. E. Street; Plant, Tissue Cell Structure; 1973; Botanical Monographs; Vol 11; pp 191–204.

Beginner's Guide to Hydroponics; Soilless Gardening; James Sholto Douglas; Consulting Member, International Working Group on Soiless Culture; Drake Publishers, Inc. N.Y. 1976.

Life Nature Library; The Plants; Frits W. Went; and Editors of Time-Life Books; N.Y.

SUMMARY OF INVENTION

FIELD OF INVENTION

The general field of the invention covers three general fields; these being the mechanical control of anaerobic fermentation; aerobic fermentation or digestion; and a new field; that of callus growth. (Live Botanical Cells).

BRIEF DESCRIPTION OF THE FIGURES

FIG. 2 illustrates a rectangular cross sectional view of the fermentation apparatus with emphasis on those structures concerned with influent and effluent handling.

FIG. 3 illustrates a side view of the fermentation apparatus.

DETAILED DESCRIPTION OF THE FIGURES

FIG. 1

Figure 1:
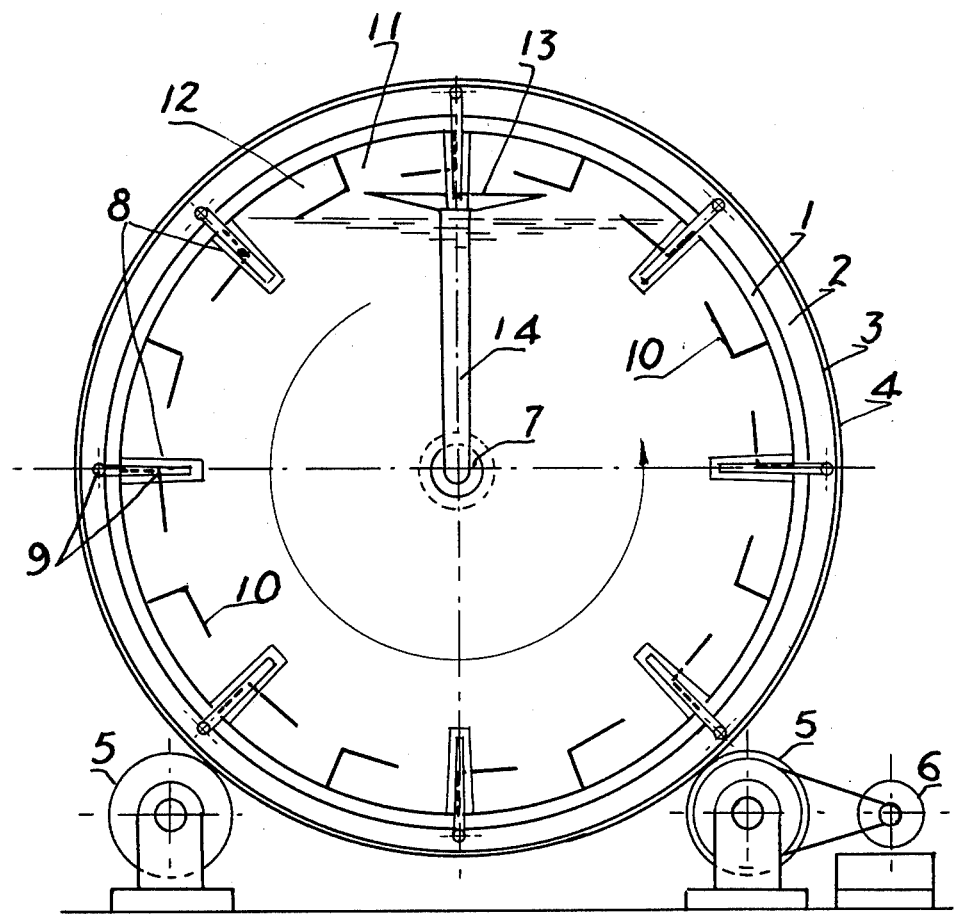
FIG. 1 illustrates a circular cross sectional view of the fermentation apparatus.

1—Drum Circumference
2—Insulation
3—Cover For Insulation

4—Outside Rim Drive Shoe of Drum
5—Bearing and Drive Wheels
6—Motor-Variable Speed
7—Influent Entry to Drum
8—Mixing Blades-Integral with Interior Drum
9—Hot or Cold Temperature Control Fluids Recirculation System
10—"Cups" on End of Drum for Solids Pick Up
11—Gases-(Volume) Space
12—Cups Trap Gases and Remix Some With Substrate
13—Hopper to Collect Cups Spill of Solids
14—Discharge Pipe for Solids

FIG. 2

1—Drum Circumfrence
7—Influent Entry To Drum
9—Hot or Cold Temperature Control Fluids Recirculation System
10—"Cups" On Drum End For Solids Pick Up
11—Gases Space
13—Hopper to Collect Cups Spill of Solids
14—Discharge Pipe For Solids
15—Clean Outs
16—Flexible-Slip-Connection
17—Coupling Connection Cap
18—Flexible-Compression Gaskets
19—Gaskets-Retainer Shoulders
20—Connection Flanges
21—Overflow For Substrate
22—High Liquid Level
23—Gas-In/Out
24—Gas Injection
25—Gas Connection

PROCESS DESCRIPTION—AEROBIC FERMENTATION

Use of the horizontal rotating drum as an aerobic treatment aerator for activated sludge requires pure oxygen or air be introduced to the drum. This is accomplished by injection along with the influent raw sewage or organic waste. Oxygen not assimilated by the liquid and its biomass solids during the process is drawn off at the effluent end of the drum in the same manner the methane is withdrawn from an anaerobic process. The oxygen is recycled back to the influent for reinjection, and thus not wasted or lost.

Aeration takes place by the mixing blades entrapping oxygen or air from the top gas phase volume in the drum and carrying it below the supernatant or substrate liquor surface for release.

Air or oxygen loading factors are previously discussed under "Summary of the Invention"—"Aerobic Fermentation."

PROCESS DESCRIPTION—CALLUS GROWTH

Use of the horizontal rotating drum as a botanical growth vessel for biological callus requires principally the addition of "Grow" lights for photosynthesis.

PHOTOSYNTHESIS

The process of Photosynthesis is very complex, requiring various enzymes in the chloroplast of plant cells to transform carbon dioxide ($CO_2$) and water ($H_2O$ into sugars.

The chloroplast must be provided sufficient radiant energy so it can perform as the cellular converter of radiant energy into chemical energy which the cell can then use as needed.

HRD DIGESTER AS A "CALLUS" VEGETATER

The principal alteration to the HRD digester, whih was originally conceived as a much more efficient expediter of anaerobic digestion can be equally efficiently growing callus cells, by addition of radiant light energy.

Light can be introduced to the process by U. V. Pyrex—double wall lamps screwed thru the vessel walls in sufficient numbers to provide the light energy required. It can also be provided by constructing windows on the drum surface behind (outside) which are light sources. Either or any method must take into consideration the cells will be attracted to the light source and block the light is some means is not provided to easily remove and/or clean the light source "windows".

OPERATION—CONTINUOUS PROCESS

The HRD—"Callus Vegetater" is the term applied to name the unit. To vegetate means "to grow after the fashion of plants".

The operation of the vegetater is to produce "Callus" cells of specific plant cells.

Callus cell "seed" or starter culture are introduced as a single water or mixture of nutrient liquor (water) and carbon dioxide saturated polyorganosiloxane fluorocarbon liquid, to the rotating drum.

As callus cells are produced they are internally pumped or caused to move by the mixing fins to the entry end of the vessel where by the mass of cells increases until they are in sufficient numbers as to be picked up in the drum "cups" and by rotation of the drum raised till they spill to the discharge hopper. They are then removed to separation of the callus and nutrient media from the silicone or fluorocarbon liquid; washed, etc.

Proper quantity of carbon dioxide and nutrients is retained in the vegetater by adjusting quantity and rate of influent nutrient media and carbon dioxide saturated silicone or fluorocarbon liquid added.

Temperature control is by temperature, rate, and quantity of hot (warm)(fluids) water circulated thru the mixing blades, and/or drum wall. (If of sandwich design).

Since Photosynthesis is required to cause Photorespiration, which occurs when photosynthetic tissues are illuminated; and from the oxidation of photosynthetic products; then the light source operates continuously, or intermitant as required.

Spent or carbon dioxide depleted suspension media of silicone or fluorocarbon overflows the discharge vent at the "down" or far end of the vegetater.

Oxygen gas, a product of photosynthesis respiration as collected above the liquids surface, being continuously stripped as formed by rotary mixing, is removed by the gas vent discharge to recovery and use.

Cooled heating fluid is removed to boiler or heat exchanger for recycle.

OPERATION—BATCH

The HDR-Vegetater can also be operated for batch or fill and drain operation by filling with pre-calculated quantities of nutrient media and carbon dioxide saturated silicone or fluorocarbon liquid; adding calculated starter cells and rotating for the time required to reproduce cell quantity designed; or until cell density reaches that desired; then draining drum of contents to separation, etc.

FERMENTER

The HDR digester or fermenter with "batch" use of drum to grow sucrose cells of plants, can immediately following production of callus be converted to a fermenter by addition of yeast. Fermentation can be continued in exactly same way the callus was produced; except light sourses can be extinguished.

Gaseous product will, as a fermenter, be carbon dioxide which is usable with other callus production.

I claim:
1. A fermentation apparatus comprising;
an aseptically sealed, horizontally rotated, cylindrically shaped drum,
supported by stiffening rings around the external circumference
which bear on external drive wheels or gears,
which cause the cylindrical drum to rotate around a horizontal axis,
ascepticity of the drum contents assured by a three fluid influent and three fluid effluent connection,
said influent connection providing fluid which is to be fermented, removing spent solid materials generated during the fermentation, and providing a heat exchanger fluid,
said effluent connection discharging fermented fluid, gases collected above the drum liquid level, and spent heat exchanging fluid,
the interior of the drum is provided with two or more parallel mounted fins in a partial spiral configuration to centerline,
mounted on interior drum walls in a manner as to connect with the heat exchanging fluid,
which enters fins at influent end of drum, and following circulation therein,
then exits fins at effluent end of drum,
the spiral action of the fins when the drum is rotated moving liquid suspended solids therein to the influent end,
cups fastened on the interior surface of the drum which during rotation lift the solids to top of drum,
said cups spill the solids to an effluent funnel and discharge pipe,
for disposal through influent rotary facility, and or a light source attached to the interior wall of the drum.

* * * * *